(12) United States Patent       (10) Patent No.:     US 8,135,477 B2
Fattouh et al.                  (45) Date of Patent:       Mar. 13, 2012

(54) NEUROSTIMULATION UTILIZING A TREE CONFIGURATION

(76) Inventors: Maher Fattouh, Madison, WI (US); David Anthony Bryce, Middleton, WI (US)

( * ) Notice: Subject to any disclaimer, the term of this patent is extended or adjusted under 35 U.S.C. 154(b) by 0 days.

(21) Appl. No.: 12/482,595

(22) Filed: Jun. 11, 2009

(65) Prior Publication Data

US 2010/0004721 A1     Jan. 7, 2010

Related U.S. Application Data

(60) Provisional application No. 61/078,495, filed on Jul. 7, 2008.

(51) Int. Cl.
*A61N 1/00*     (2006.01)

(52) U.S. Cl. ........................................ 607/117

(58) Field of Classification Search ........... 600/372; 606/129; 607/116, 117, 122, 126, 2, 29, 607/63
See application file for complete search history.

(56) References Cited

U.S. PATENT DOCUMENTS

| | | | |
|---|---|---|---|
| 6,453,198 B1 * | 9/2002 | Torgerson et al. | 607/29 |
| 2005/0096718 A1 | 5/2005 | Gerber et al. | |
| 2005/0222658 A1 * | 10/2005 | Hoegh et al. | 607/116 |
| 2006/0089691 A1 * | 4/2006 | Kaplan et al. | 607/116 |
| 2006/0206183 A1 | 9/2006 | Pyles et al. | |
| 2007/0027514 A1 * | 2/2007 | Gerber | 607/116 |
| 2007/0055307 A1 | 3/2007 | Pyles | |
| 2007/0112398 A1 * | 5/2007 | Stevenson et al. | 607/63 |
| 2008/0154329 A1 | 6/2008 | Pyles | |
| 2008/0161886 A1 * | 7/2008 | Stevenson et al. | 607/60 |
| 2008/0269863 A1 | 10/2008 | Alexander et al. | |
| 2009/0112281 A1 | 4/2009 | Miyazawa et al. | |
| 2009/0276025 A1 * | 11/2009 | Burnes et al. | 607/126 |

* cited by examiner

*Primary Examiner* — George Manuel
*Assistant Examiner* — Robert Wieland
(74) *Attorney, Agent, or Firm* — Terra Nova Patent Law, PLLC; Mitchell A. Rossman (57) ABSTRACT

A neurostimulator conduit introducer is provided. The neurostimulator conduit introducer includes a central lead having a proximal end and a distal end; one or more secondary leads each having a proximal end and a distal end; and a biocompatible conduit enclosing the central lead and the one or more secondary leads, wherein the biocompatible conduit is moveable along the central lead and the one or more secondary leads. Methods of using the neurostimulator conduit introducer and kits including the neurostimulator conduit introducer are also provided.

15 Claims, 12 Drawing Sheets

NEUROSTIMULATION UTILIZING A TREE CONFIGURATION

RELATED APPLICATIONS

This application claims priority to U.S. Provisional Patent Application Ser. No. 61/078,495, filed Jul. 7, 2008, which is hereby incorporated by reference in its entirety for all purposes.

BACKGROUND OF THE INVENTION

Implantable medical devices may be used to deliver electrical stimulation therapy to patients to treat a variety of symptoms or conditions, for example, chronic pain, tremor, Parkinson's disease, epilepsy, incontinence, or gastroparesis. Electrical stimulation therapy may be applied to deliver stimulation to any of a variety of tissue sites and may comprise, for example, neurostimulation, stimulation of muscle tissue, or the like. A medical device may deliver electrical stimulation therapy via a stimulator generator and one or more implantable leads that include electrodes located proximate to the spinal cord, pelvic nerves, stomach, or within the brain of a patient. The stimulation generator may be external or implantable. For chronic therapy, an implantable stimulation generator is typically desirable. In general, the medical device delivers electrical stimulation therapy in the form of electrical pulses, although continuous waveforms alternatively or additionally may be applied.

Spinal cord stimulation is used to alleviate chronic pain by stimulating the central nervous system using electrode arrays. Conventional spinal cord stimulator leads include percutaneous leads and surgical leads. Percutaneous leads are solid and have typically, four or eight electrodes. The percutaneous leads can be inserted through a needle and placed in the epidural space, in close proximity to the spinal cord. When activated, the electrodes deliver a precise, mild electrical impulse to the spinal cord or to a peripheral nerve. The electrical impulses activate pain inhibitory mechanisms to block the pain signal from reaching the brain.

Current designs of electrode arrays have had particular problems including, for example, lead migration, variable stimulation, and an inability to consistently stimulate deep fibers in the spinal cord. The stimulation of deeper midline structures is essential for treating low back pain. Further, multiple leads are required to cover large painful areas.

BRIEF DESCRIPTION OF THE DRAWINGS

Embodiments of the invention may be best understood by referring to the following description and accompanying drawings, which illustrate such embodiments. In the drawings.

The drawings are not necessarily to scale. Like numbers used in the figures refer to like components, steps and the like. However, it will be understood that the use of a number to refer to a component in a given figure is not intended to limit the component in another figure labeled with the same number.

SUMMARY OF THE INVENTION

The present invention provides a neurostimulator conduit introducer for placement. The neurostimulator conduit introducer has a unique design that includes a central lead having a proximal end and a distal end; one or more secondary leads each having a proximal end and a distal end; and a biocompatible conduit enclosing the central lead and the one or more secondary leads. The biocompatible conduit can be moved along the central lead and the secondary leads.

This neurostimulator conduit introducer provides many unique advantages including, for example, the ability to easily regulate the number and the three-dimensional structure of the exposed leads, the ability to resist migration of the leads due to bodily movements, the ability to provide wider coverage of the pain area and for a longer time and therefore negating the need to place more than one lead in the pain area, avoiding the revision of the designs that incorporate a single lead, more programmable flexibility than designs with single leads because of the three-dimensional area of the secondary leads.

The number and the three-dimensional structure of exposed leads are controlled by the extent that the biocompatible conduit is moved toward the proximal end of the neurostimulator conduit introducer. A small movement of the biocompatible conduit exposes a small number of leads toward the distal end of the neurostimulator conduit introducer that assume a small three-dimensional tree-like space; whereas a large movement of the biocompatible conduit exposes a large number of leads toward the distal end of the neurostimulator conduit introducer that assume that assume a large three-dimensional tree-like space. This adjustable arrangement provides great flexibility for stimulating the spinal cord.

Another advantage of the neurostimulator conduit introducer is the ability to resist migration of the leads caused by bodily movements. The neurostimulator conduit introducer contains leads that are coiled inside the biocompatible conduit. For example, when the spinal cord is flexed, the coiled leads remove the shear stress by lengthening inside the biocompatible conduit.

As such, the neurostimulator conduit introducer provides leads that cover a wider three-dimensional area and have less chance of migrating. This results in better patient and physician satisfaction.

The present invention provides a neurostimulator conduit introducer for placement. The neurostimulator conduit introducer includes a central lead having a proximal end and a distal end; one or more secondary leads each having a proximal end and a distal end; and a biocompatible conduit enclosing the central lead and the one or more secondary leads, wherein the biocompatible conduit is moveable along the central lead and the one or more secondary leads.

In one embodiment, the neurostimulator is a spinal cord stimulator, a pelvic nerve stimulator, a deep brain stimulator, a gastrointestinal stimulator, a peripheral nerve stimulator, a vascular stimulator, or a muscle stimulator. In another embodiment, the neurostimulator is a spinal cord stimulator.

In one embodiment, each of the one or more secondary leads has a different length. In another embodiment, some of the one or more secondary leads have the same length.

In one embodiment, each of the one or more secondary leads is independently wrapped around the central lead. In another embodiment, each of the one or more secondary leads includes an electrode.

In one embodiment, the electrode is located on distal end of each of the one or more secondary leads. In another embodiment, the electrode includes a concave surface that is complementary to a surface of the central lead. In yet another embodiment, the biocompatible conduit is movable toward the proximal ends of the central lead and the one or more secondary leads to expose a part of the central lead and a part of the one or more secondary leads.

In one embodiment, the biocompatible conduit is movable toward the distal ends of the central lead and the one or more secondary leads to cover a part of the central lead and a part of the one or more secondary leads. In another embodiment, the proximal end of the central lead is coiled inside the biocompatible conduit, the proximal end of each one or more secondary leads is coiled inside the biocompatible conduit, or both the proximal end of the central lead and the proximal end of each one or more secondary leads are each independently coiled inside the biocompatible conduit.

In one embodiment, the neurostimulator conduit introducer further includes a battery coupled to the electrodes. In another embodiment, the battery is rechargeable. In yet another embodiment, the battery includes a capacitor, a microchip, or a combination thereof.

The present invention also provides a method of implanting a neurostimulator conduit introducer. This method includes: inserting a neurostimulator conduit introducer including: a central lead having a proximal end and a distal end; one or more secondary leads each having a proximal end and a distal end; and a biocompatible conduit enclosing the central lead and the one or more secondary leads, wherein the biocompatible conduit is moveable along the central lead and the one or more secondary leads; and guiding the neurostimulator conduit introducer into a desired position.

In one embodiment, the neurostimulator is a spinal cord stimulator, a pelvic nerve stimulator, a deep brain stimulator, a gastrointestinal stimulator, a peripheral nerve stimulator, a vascular stimulator, or a muscle stimulator. In another embodiment, the neurostimulator is a spinal cord stimulator.

In one embodiment, the method further includes moving the biocompatible conduit toward the proximal ends of the central lead and the one or more secondary leads to expose a part of the central lead and a part of the one or more secondary leads. In another embodiment, the exposed secondary leads are located both along the central lead and laterally away from central lead.

In one embodiment, the method further includes moving the biocompatible conduit toward the terminal ends of the central lead and the one or more secondary leads to cover a part of the central lead and a part of the one or more secondary leads. In another embodiment, the covered secondary leads are located along the central lead.

In one embodiment, the method further includes using fluoroscopy to guide placement of the neurostimulator conduit introducer. In another embodiment, the method further includes suturing the neurostimulator conduit introducer in the desired position in the epidural space.

The present invention provides a kit. The kit includes a needle; a sterile drape; a neurostimulator conduit introducer including: a central lead having a proximal end and a distal end; one or more secondary leads each having a proximal end and a distal end; and a biocompatible conduit enclosing the central lead and the one or more secondary leads, wherein the biocompatible conduit is moveable along the central lead and the one or more secondary leads; and suturing supplies.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass, 1993, and *The American Heritage Dictionary of the English Language*, Houghton Mifflin, Boston Mass., 1981.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example, about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "biocompatible" refers to the material, substance, compound, molecule, polymer, or system, which does not cause severe toxicity, severe adverse biological reaction, or lethality in an animal when administered at reasonable doses and rates.

As used herein, the term "in communication" refers to the stimulation lead being adjacent, in the general vicinity, in close proximity, or directly next to or directly on the predetermined stimulation site, for example, a level or area of the spinal cord associated with thoracic vertebral segments. Thus, one of skill in the art understands that the lead is "in communication" with the nervous tissue or spinal cord associated with a thoracic vertebral segment if the stimulation results in a modulation of neuronal activity resulting in the desired response.

As used herein, the terms "epidural space" or "spinal epidural space" refer to an area in the interval between the dural sheath and the wall of the spinal canal.

As used herein, the term "flexible" refers to a neurostimulator conduit introducer that is compliant and readily conforms to the general shape and contours of the tissues and parts of, for example, the human body. In some embodiments, the neurostimulator conduit introducer is flexible.

As used herein, the terms "include," "for example," "such as," and the like are used illustratively and are not intended to limit the present invention.

As used herein, the terms "individual," "host," "subject," and "patient" are used interchangeably, and refer to a mammal, including, but not limited to, primates, including simians and humans.

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, for example, horses, cattle, sheep, and goats, and research and domestic species, including dogs, cats, mice, rats, guinea pigs, and rabbits.

As used herein, the term "patient" refers to a warm-blooded animal, and preferably a mammal, for example, a cat, dog, horse, cow, pig, mouse, rat, or primate, including a human.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "proximal" and "distal" refer to position relative to a neurostimulator conduit introducer, a central lead, and/or a secondary lead. For example, a proximal portion of a neurostimulator conduit introducer is a portion nearer a battery, and a distal portion is a portion further from the battery As used herein, the terms "signal generator" and "pulse generator" are used interchangeably. It will be understood that a pulse generator may generate an electrical signal or a plurality of electrical signals that are not pulses.

As used herein, the phrase "spinal cord stimulation" refers to stimulation of any spinal nervous tissue, including spinal neurons, accessory neuronal cells, nerves, nerve roots, nerve fibers, or tissues that are associated with the spinal cord.

As used herein, the phrase "spinal nervous tissue" refers to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord. Spinal nervous tissue includes "spinal nerve roots," which include the 31 pairs of nerves that emerge from the spinal cord. Spinal nerve roots may be cervical nerve roots, thoracic nerve roots, and lumbar nerve roots.

As used herein, the term "subdural" refers to the space between the dura matter and arachnoid membrane.

As used herein, the terms "therapy," and "therapeutic" refer to either "treatment" or "prevention," thus, agents that either treat damage or prevent damage are "therapeutic."

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease.

As used herein, the term "treatment," covers any treatment of a disease in a mammal, particularly in a human, and includes: (a) preventing the disease from occurring in a subject which may be predisposed to the disease but has not yet been diagnosed as having it; (b) inhibiting the disease, that is, arresting its development; and (c) relieving the disease, that is, causing regression of the disease.

The present invention provides a neurostimulator conduit introducer. The neurostimulator conduit introducer has a unique design that includes a central lead having a proximal end and a distal end; one or more secondary leads each having a proximal end and a distal end; and a biocompatible conduit enclosing the central lead and the one or more secondary leads. The biocompatible conduit can be moved along the central lead and the secondary leads.

Figure 1:
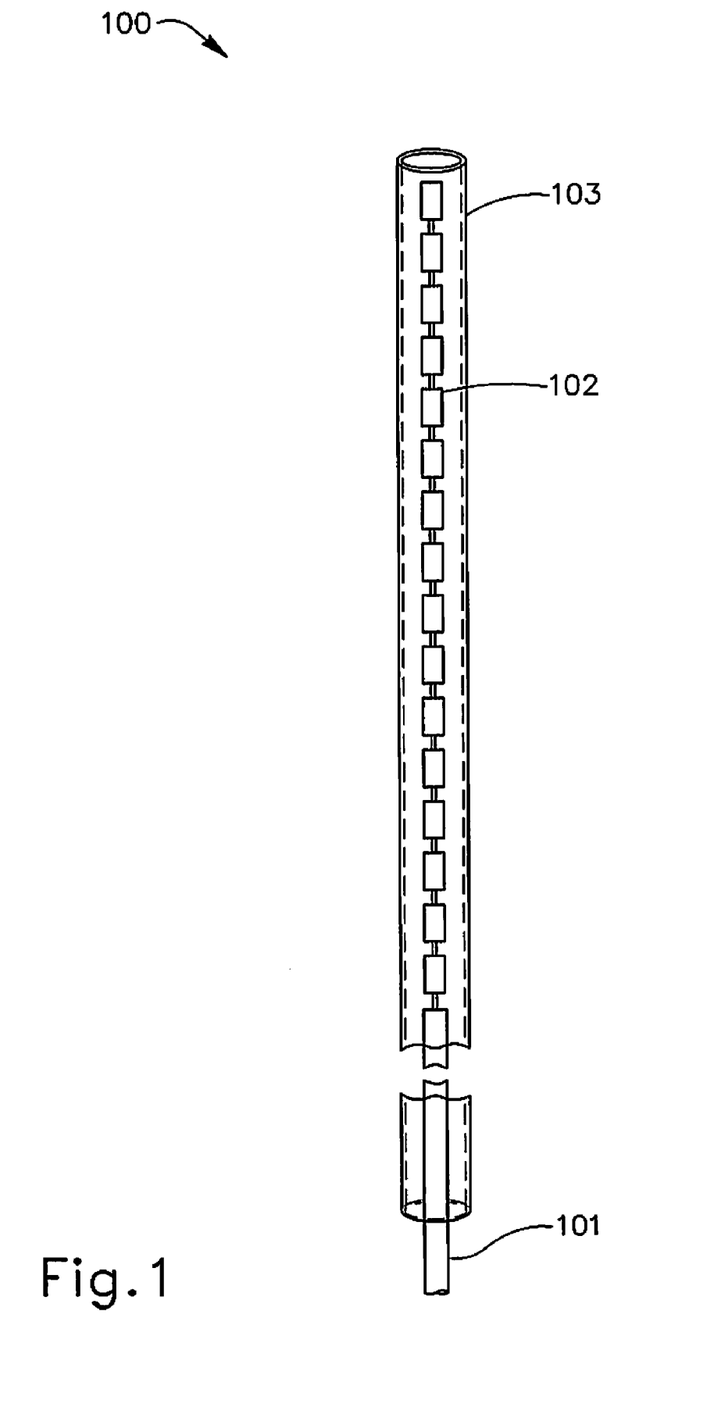
FIG. 1 is a drawing illustrating an exemplary neurostimulator conduit introducer.

FIG. 1 illustrates an exemplary neurostimulator conduit introducer 100 that includes, for example, an internal or central lead 101, simulator poles or secondary leads 102, and a biocompatible conduit 103. The central lead 101 is typically larger in diameter than the secondary leads 102. When the neurostimulator conduit introducer 100 is in the closed position, as shown in FIG. 1, the central lead 101 and the secondary leads 102 are positioned tightly inside the biocompatible conduit 103. Further, a tension exists between the central lead 101 and the secondary leads 102. When the biocompatible conduit 103 is moved toward the proximal end of the neurostimulator conduit introducer 100 and exposes some of the secondary leads 102, the tension between the central lead 101 and the secondary leads 102 may cause some of the secondary leads 102 to unfold away from the central lead 101. Therefore, by varying the position of the biocompatible conduit 103, the number of exposed secondary leads 102 and the degree of branching of some of the secondary leads 102 from the central lead 101 may be controlled. This arrangement provides adjustable control of the stimulation of the neural structures.

The central lead 101 and the secondary leads 102 may be of any desired length. Appropriate selection of the central lead 101 and the secondary leads 102 size can be made in accordance with accepted medical protocol as determined by the treating physician.

Optionally, the neurostimulator conduit introducer 100 includes a surface marker (not shown), for example, a radiographic strip or band that is near the tip of the neurostimulator conduit introducer 100. In one embodiment, the marker is on the outside of the biocompatible conduit 103. The marker can aid the practitioner in guiding the neurostimulator conduit introducer 100 under fluoroscopy or other conventional imaging techniques into a proper placement in the desired space.

The neurostimulator conduit introducer, as described herein. may be made according to any known or future developed process. For example, the biocompatible conduit 103 may be injection molded or extruded. In some situations it may be desirable to reflow the biocompatible conduit 103 from thermoplastic polymers.

The biocompatible conduit 103 may be made of, for example, polyurethane, polystyrene, polyvinylchloride, polyacrylates, silicone, silicone rubbers, silicone elastomers, silicone gel, polymers of ethylene-vinyl acetates and other acyl substituted cellulose acetates, polyvinyl fluoride, poly (vinyl imidazole), chlorosulphonate polyolefins, polyethylene oxide, and homopolymer or copolymer blends thereof. Those skilled in the art will understand that various other biocompatible or biologically inert materials of construction can be used as well, without deviating from the scope of the present invention.

The central lead, each of the secondary leads, and the electrodes may be formed of electrically conductive biocompatible materials, for example, platinum, platinum iridium, titanium, tantalum, nickel-cobalt-chromium-molybdenum alloys, or the like. The central lead and/or each of the secondary leads may include, for example, braided strand wire.

Figure 2:
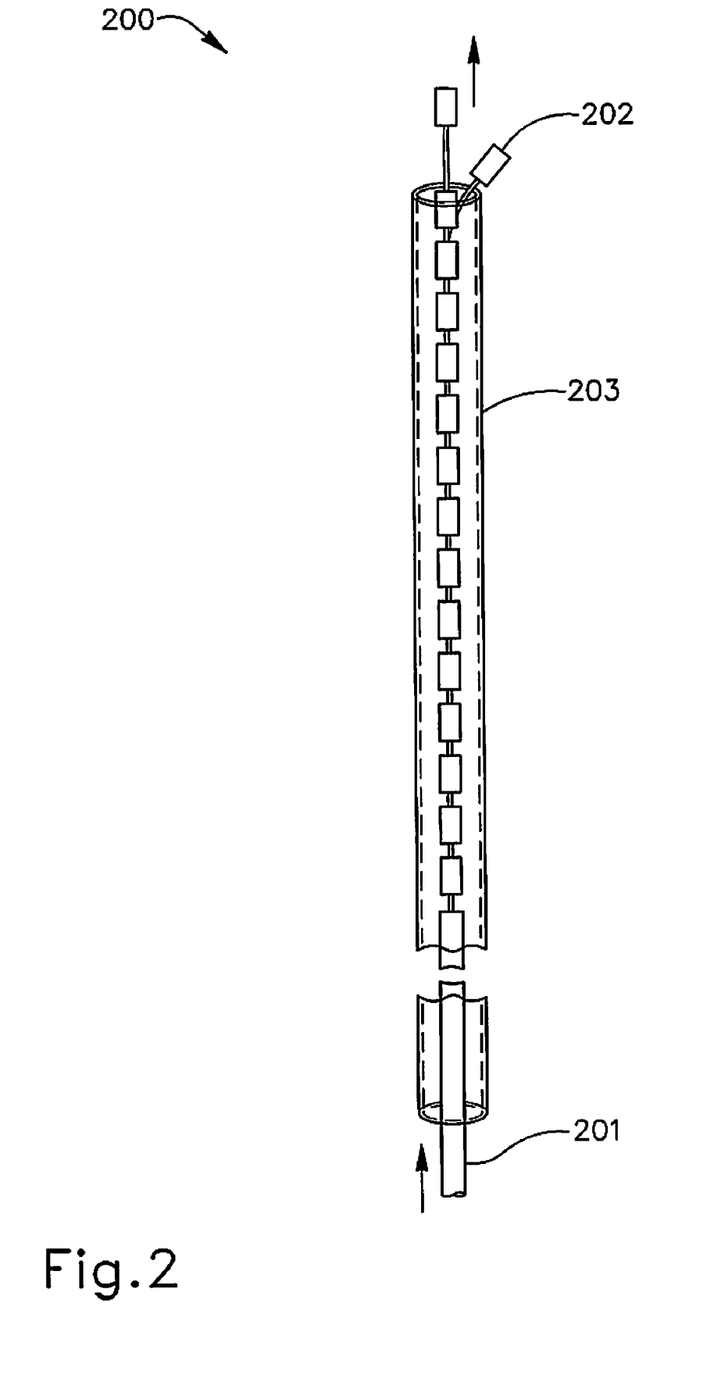
FIG. 2 is a drawing illustrating an exemplary neurostimulator conduit introducer in which the biocompatible conduit has been moved exposing one or more branched leads.

FIG. 2 illustrates an exemplary neurostimulator conduit introducer 200 in which a portion of the biocompatible conduit 203 has been moved toward the proximal end of the neurostimulator conduit introducer 200 to expose some of the secondary leads 202. When this happens, some of the secondary leads 202 may unfold away from the central lead 201.

Figure 3:
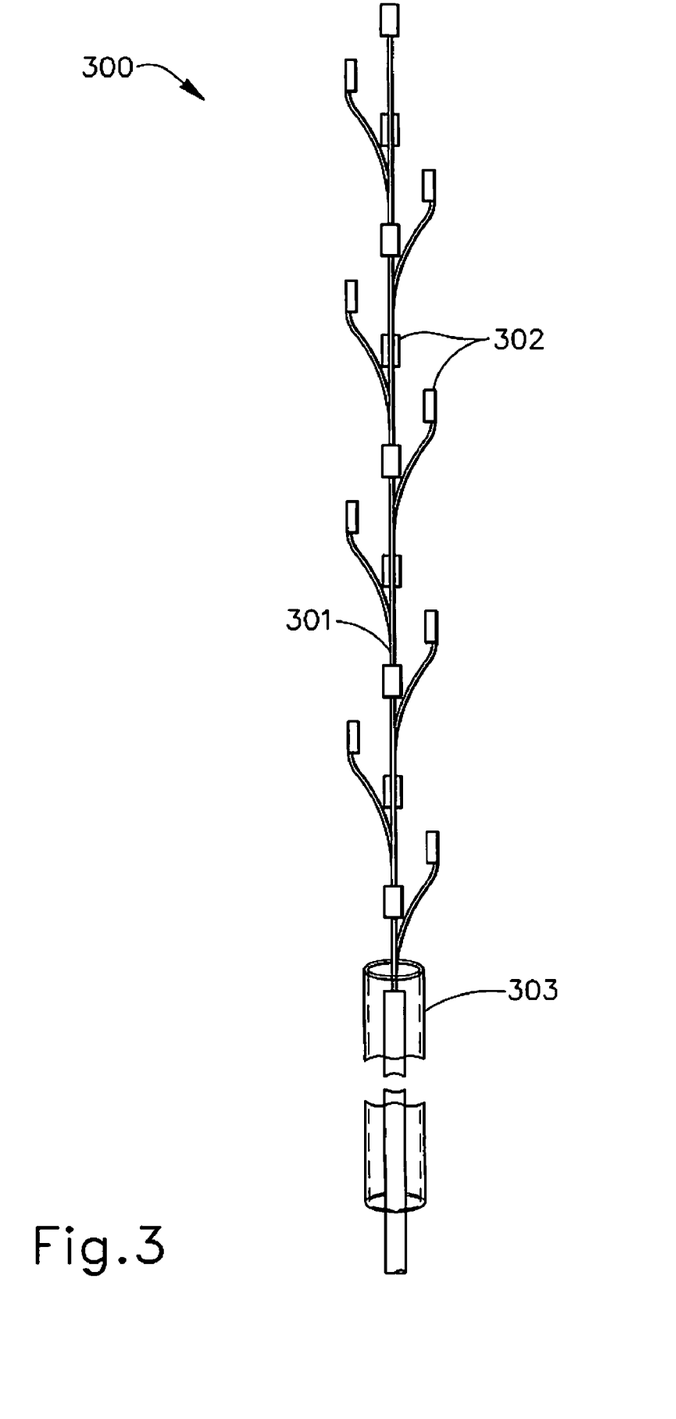
FIG. 3 is a drawing illustrating an exemplary neurostimulator conduit introducer in which the biocompatible conduit has been moved exposing one or more branched leads.

FIG. 3 illustrates an exemplary neurostimulator conduit introducer 300 in which a portion of the biocompatible conduit 303 has been moved toward the proximal end of the neurostimulator conduit introducer 300 to expose all of the secondary leads 302. When this happens, some of the secondary leads 302 may unfold away from the central lead 301. Further, some of the secondary leads 302 may remain aligned with the central lead 301. As such, a three-dimensional array of secondary leads 302 in the epidural space.

Figure 4:
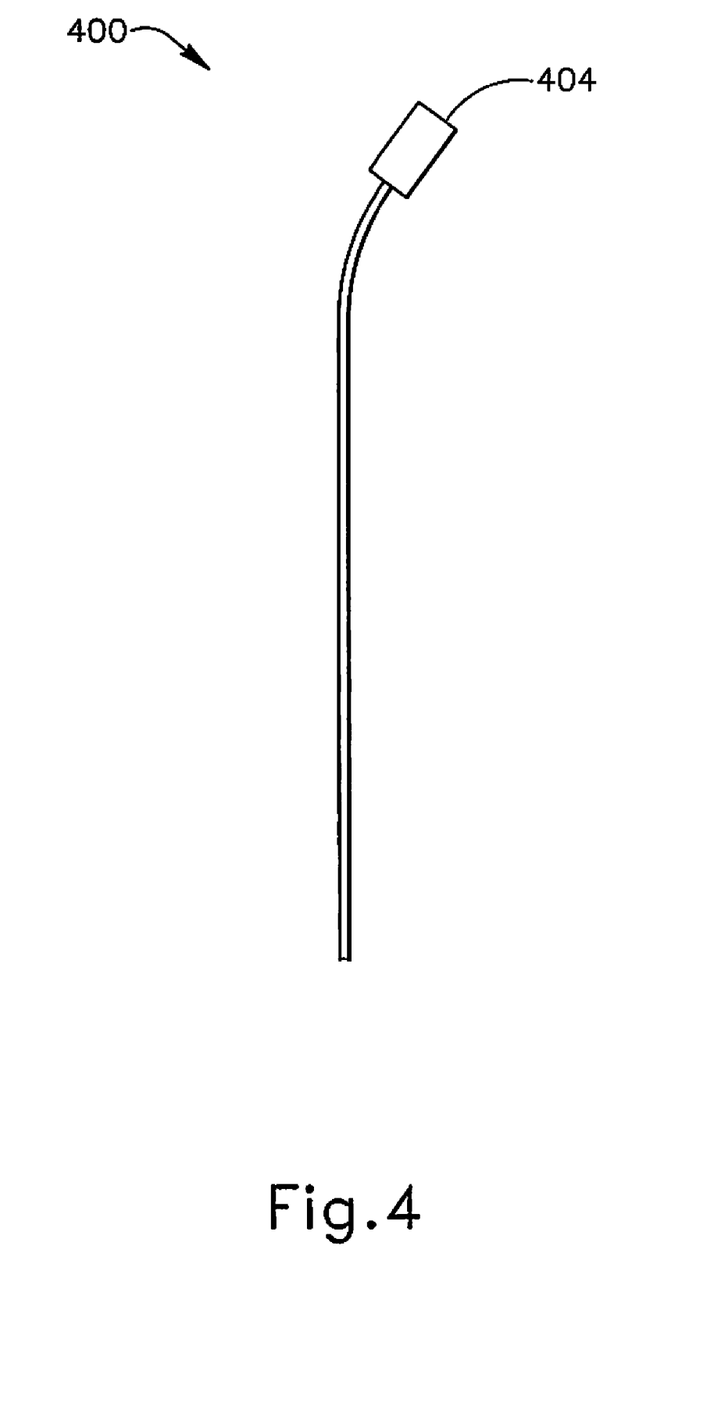
FIG. 4 is a drawing illustrating an exemplary branched lead.

FIG. 4 illustrates an exemplary secondary lead 400. The secondary lead 400 is composed of a flexible stiff material that has a preshaped angle near the electrode 401. In one embodiment, a portion of the secondary leads do not have a preshaped angle near the electrode. That is, some of the secondary electrodes are straight. In this case, the neurostimulator conduit introducer is made up of bent and straight secondary leads. This combination provides for the configuration of straight and bent secondary leads as shown in FIG. 3.

Figure 5A:
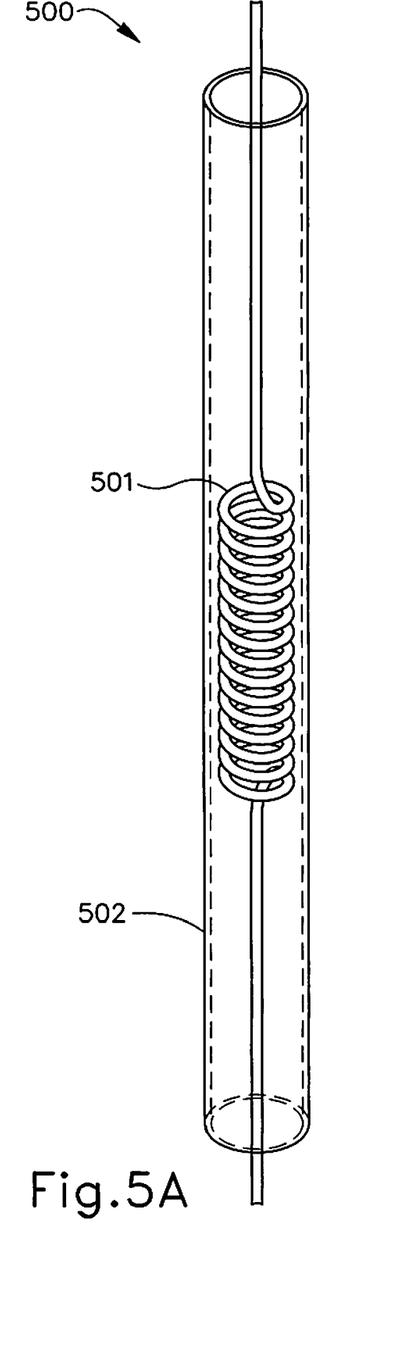
FIG. 5 is a drawing illustrating an exemplary neurostimulator conduit introducer with tension and without tension.
Figure 5B:
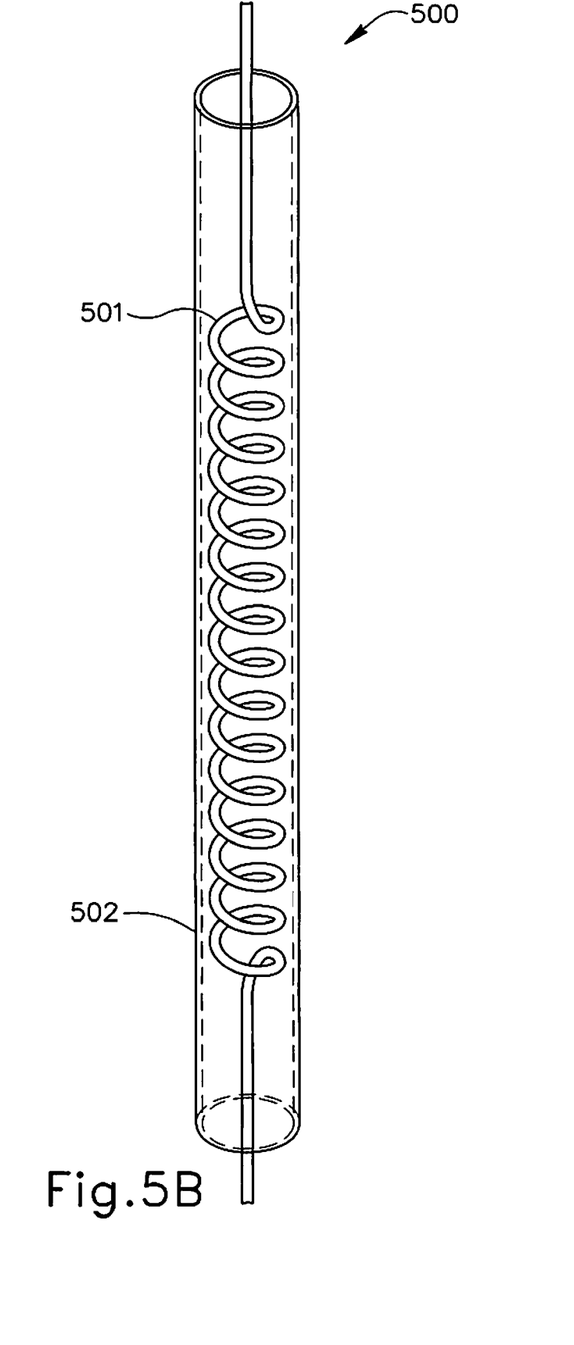

FIG. 5 illustrates the effect of tension on one of the leads, for example, the central lead and/or one of the secondary leads. For example, when the neurostimulator conduit introducer 500 is not under tension (right side of FIG. 5); the lead 501 is coiled within the biocompatible conduit 502. When tension is applied (see left side of FIG. 5), the length of the lead 501 is lengthened to absorb the tension.

Figure 6:
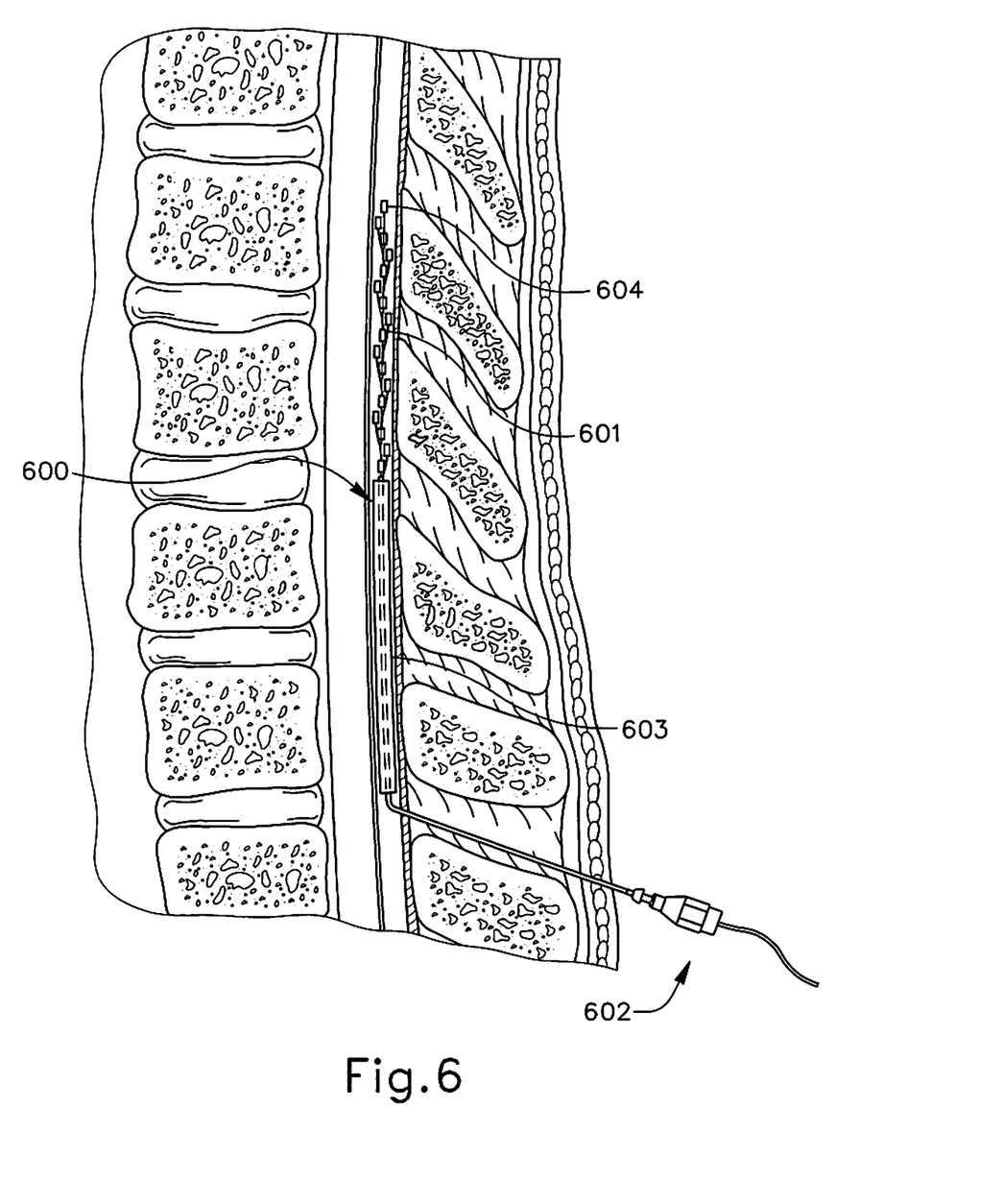
FIG. 6 is a drawing illustrating an exemplary neurostimulator conduit introducer placed inside the epidural space.

FIG. 6 illustrates an exemplary neurostimulator conduit introducer 600 placed inside the epidural space 601. The neurostimulator conduit introducer 600 is introduced into the epidural space 601 via a syringe 602. Once in place in the epidural space 601, the biocompatible conduit 603 is moved toward the proximal end of neurostimulator conduit introducer 600 to uncover a portion of the central lead and a portion of the secondary leads 604. As a result, a three-dimensional array of the electrodes on the uncovered secondary leads 604 is formed. Moving the biocompatible conduit 603 farther away from the electrodes at the tips of the secondary leads 604 allows the electrodes to spread more laterally from the central lead, thereby branching out in a tree-like pattern.

Figure 7:
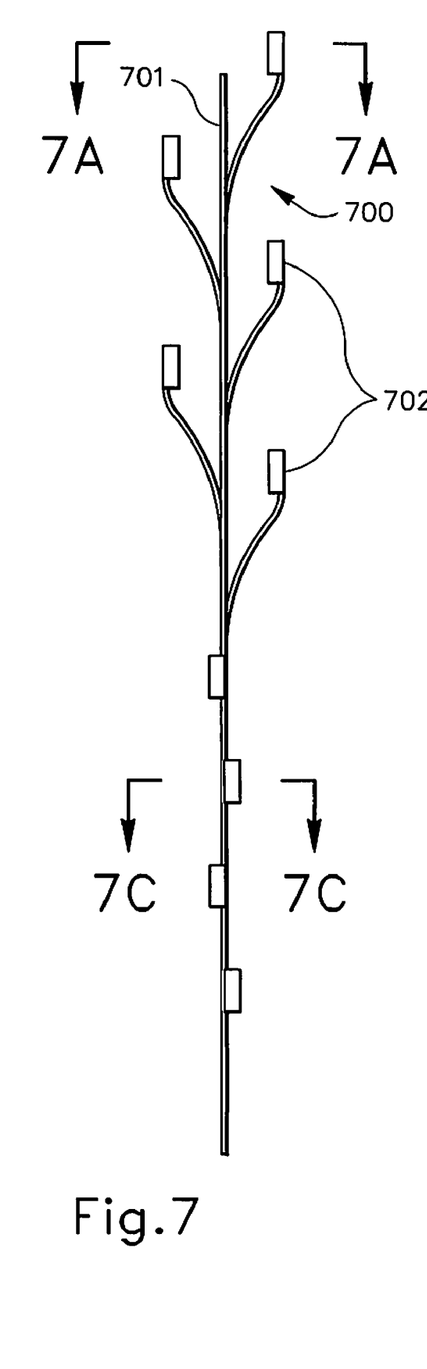
FIG. 7 is a drawing illustrating one or more exemplary branched leads wrapped around a central lead. A superior cross section of an exemplary electrode, an interior view of an exemplary electrode, and a superior cross section of an electrode and axis wire are also shown.
Figure 7A:
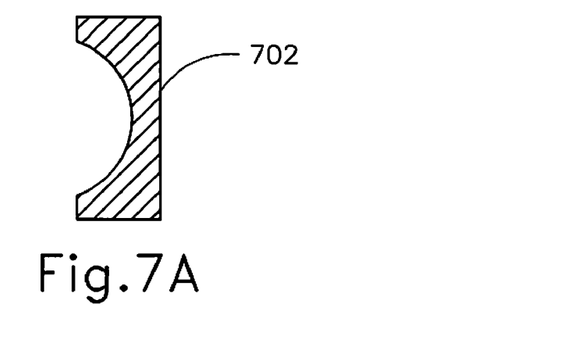
Figure 7B:
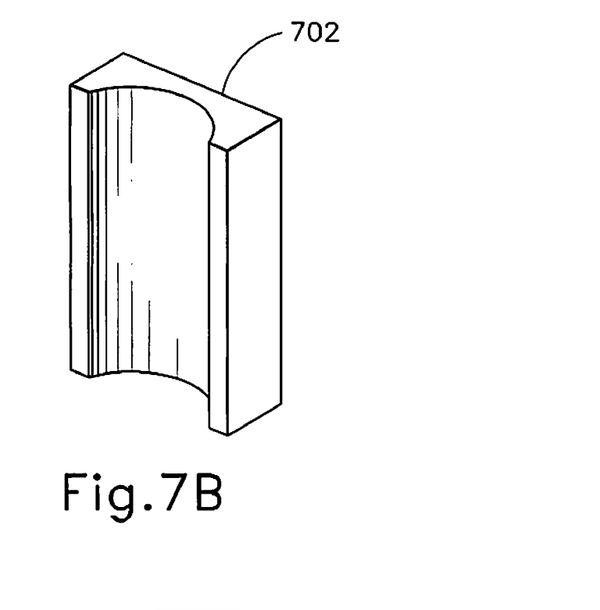
Figure 7C:
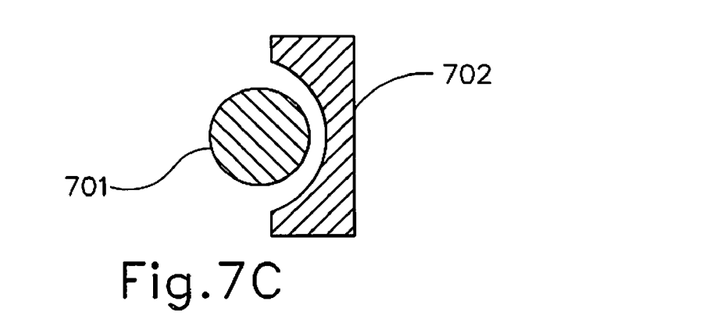

FIG. 7 illustrates exemplary branched leads 700 wrapped around a central lead 701. In the proximal portion of this combination, the branched leads 700 are held snug to the central lead 701 by the biocompatible conduit (not shown). The electrodes 702 have a concave shape which forms a complementary fit with the central lead 701. After the biocompatible conduit (not shown) is moved toward the proximal end of the central lead 701, the spring force exerted on the branched leads 700 causes them to extend into a three-dimensional array tree-like pattern. In this embodiment, all of the electrodes 702 are shown in a pattern away from the central lead 701. However, in other embodiments, some of the electrodes 702 remain in place on the central lead 701 as shown in FIG. 3.

FIG. 7 also illustrates a superior cross section of an exemplary electrode 702A, an interior view of an exemplary electrode 702B, and a superior cross section of an electrode 702C and central lead 701A.

Figure 8:
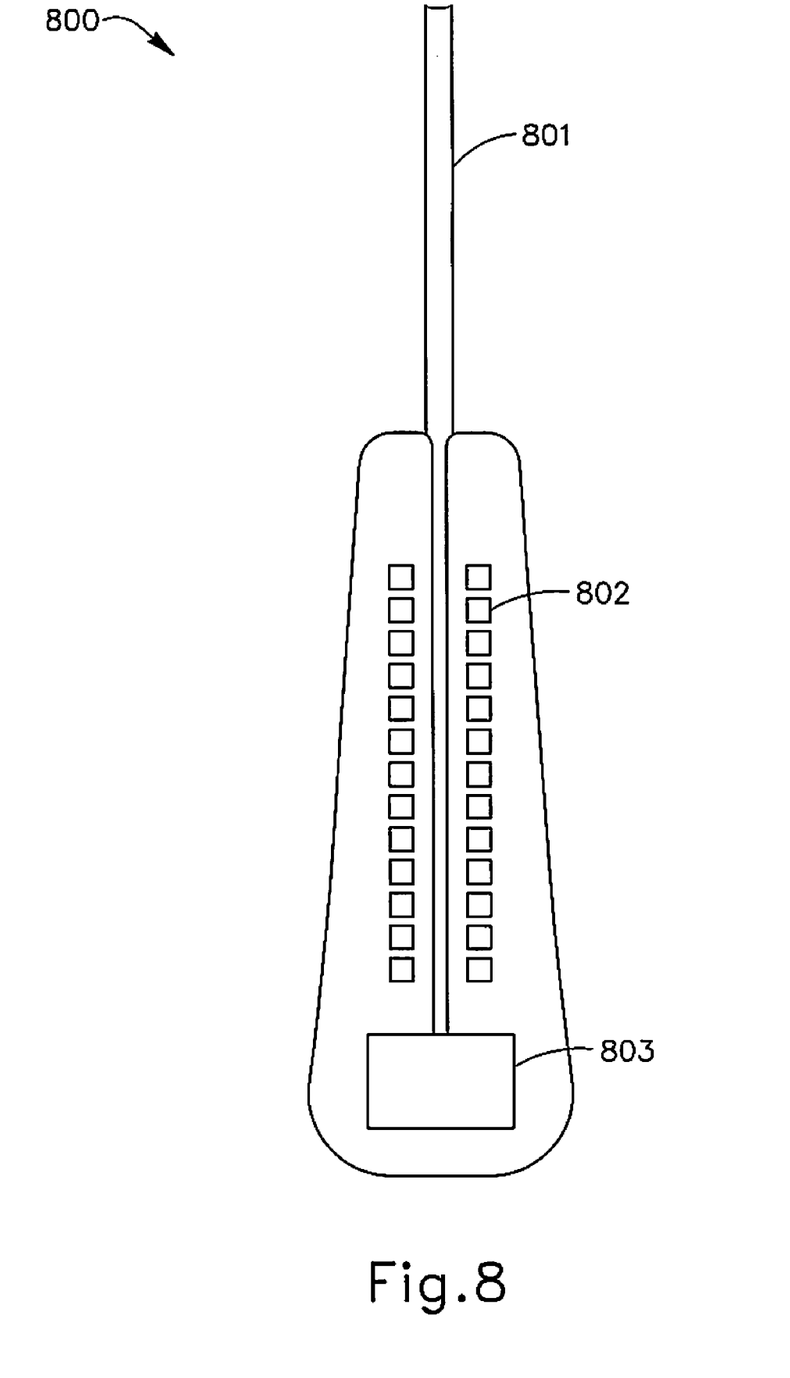
FIG. 8 is a drawing illustrating an exemplary rechargeable battery connected to the leads.

FIG. 8 illustrates an exemplary rechargeable battery 800 connected to the lead 801. The rechargeable battery 800 may include, for example, a microchip 802 to store data and a capacitor 803. The capacitor 803 may be charged by transdermal conduction. The rechargeable battery 800 may be placed in the subcutaneous space in a paramedian position without having to make another incision in another location. Further, when the rechargeable battery 800 is placed near the leads, there is no need for connectors and cables that may lead to stay capacitance and potential areas that could malfunction.

Figure 9A:
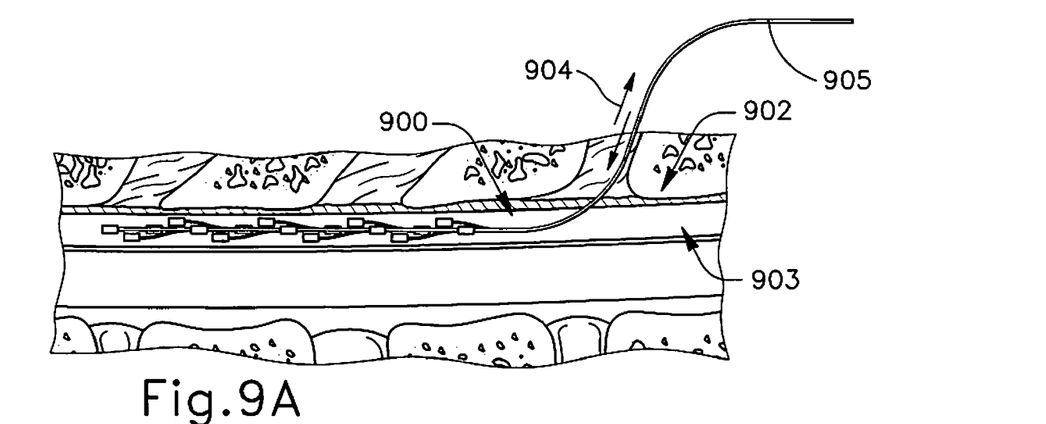
FIG. 9 is a drawing illustrating the effect of shear force on a prior art neurostimulator and an exemplary neurostimulator conduit introducer.
Figure 9B:
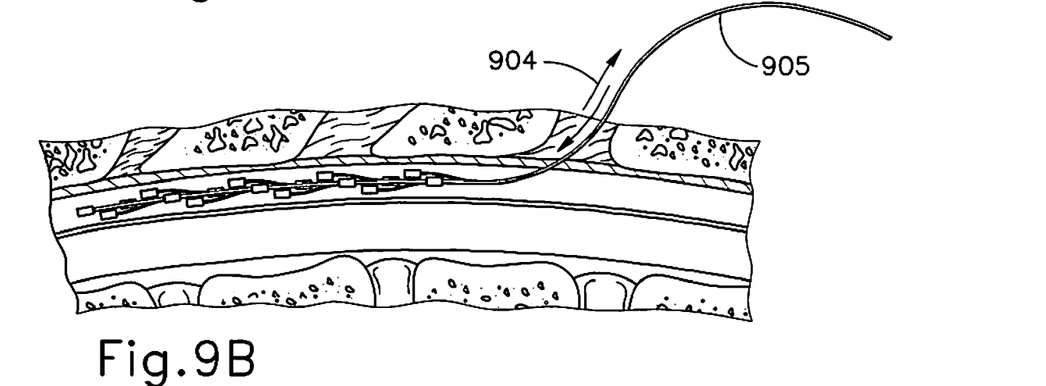
Figure 9C:
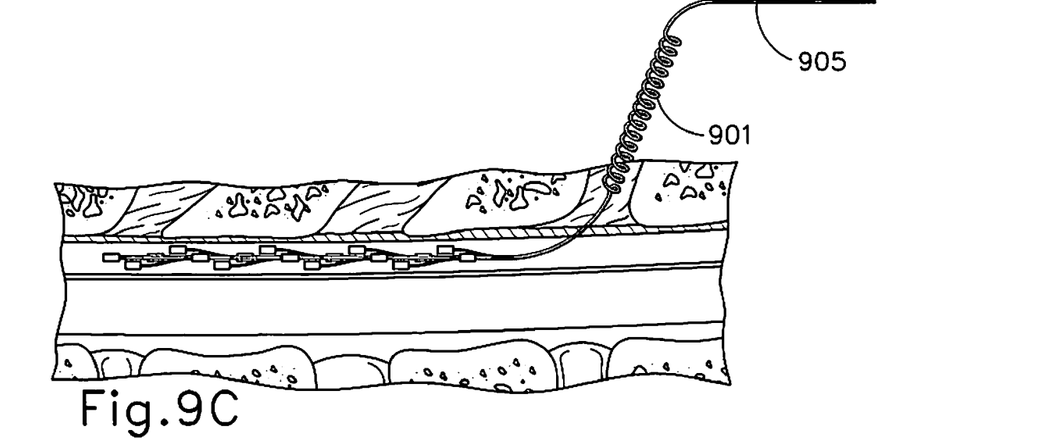

FIG. 9 illustrates the effect of shear force on a prior art neurostimulator 900 and an exemplary neurostimulator conduit introducer 901. FIG. 9A shows a prior art neurostimulator 900 inserted through the ligamentum flavum ligament 902 and into the epidural space 903 in resting position with very low shear forces 904. When the spine is arched as in FIG. 9B, the motion increases the shear forces 904 on the prior art neurostimulator 900 and results in the lead 905 separating from the surface of the patient. FIG. 9C shows an exemplary neurostimulator conduit introducer 901 in which the lead is coiled. Upon application of motion, the spring lengthens and dissipates the stress on the lead 905. As a result, the lead 905 does not separate from the surface of the patient.

Figure 10:
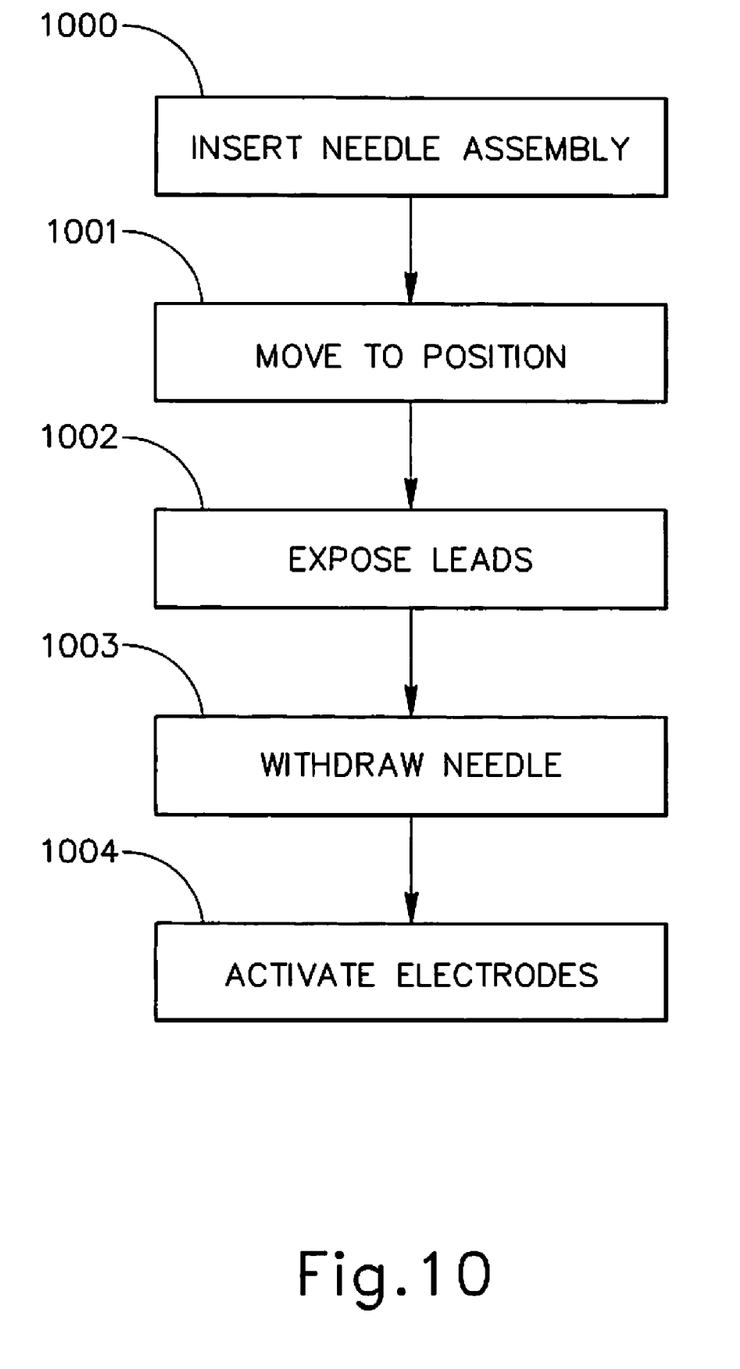
FIG. 10 is a flow diagram illustrating implantation and use of an exemplary neurostimulator conduit introducer.

FIG. 10 is a flow diagram illustrating implantation and use of an exemplary neurostimulator conduit introducer. A needle assembly is inserted into a patient. The needle assembly may include, for example, a needle and an exemplary neurostimulator conduit introducer fitted into a lumen defined by the needle. The lumen may have a diameter, for example, between about 14 and about 20 gauge to allow the needle to receive the exemplary neurostimulator conduit introducer. The neurostimulator conduit introducer may fill the lumen of the needle, preventing tissue coring. In some embodiments, for example, for epidural applications, the needle may include a modified Tuohy needle, which has an opening that is angled approximately 45 degrees so that an instrument passing through the needle exits at an angled.

The exemplary neurostimulator conduit introducer may be inserted 1000 by a variety of techniques not limited to the technique described above. The exemplary neurostimulator conduit introducer is inserted into the patient and advances until it reaches the therapy target site. Once the exemplary neurostimulator conduit introducer reaches the therapy target site, the biocompatible conduit is moved toward the proximal end of the exemplary neurostimulator conduit introducer 1001. At this time, some of the secondary leads may unfold away from the central lead to provide a three-dimensional array of electrodes 1002. The needle may be removed from the patient 1003 and exemplary neurostimulator conduit introducer may be activated may be activated 1004 to provide therapy to the patient.

Therapy may require that the exemplary neurostimulator conduit introducer be activated for only a short period of time, for example, for trial stimulation, sometimes referred to as screening. On the other hand, therapy may require that the exemplary neurostimulator conduit introducer be implanted chronically for a number of years. In either case, it may become necessary to remove the exemplary neurostimulator conduit introducer from the patient. At that time, the biocompatible conduit is moved toward the distal end of the exemplary neurostimulator conduit introducer. This movement results in the collapse of the three-dimensional tree-like array of electrodes as the electrode return to the center lead and are enclosed by the advancing biocompatible conduit. Finally, the exemplary neurostimulator conduit introducer is withdrawn.

Figure 11:
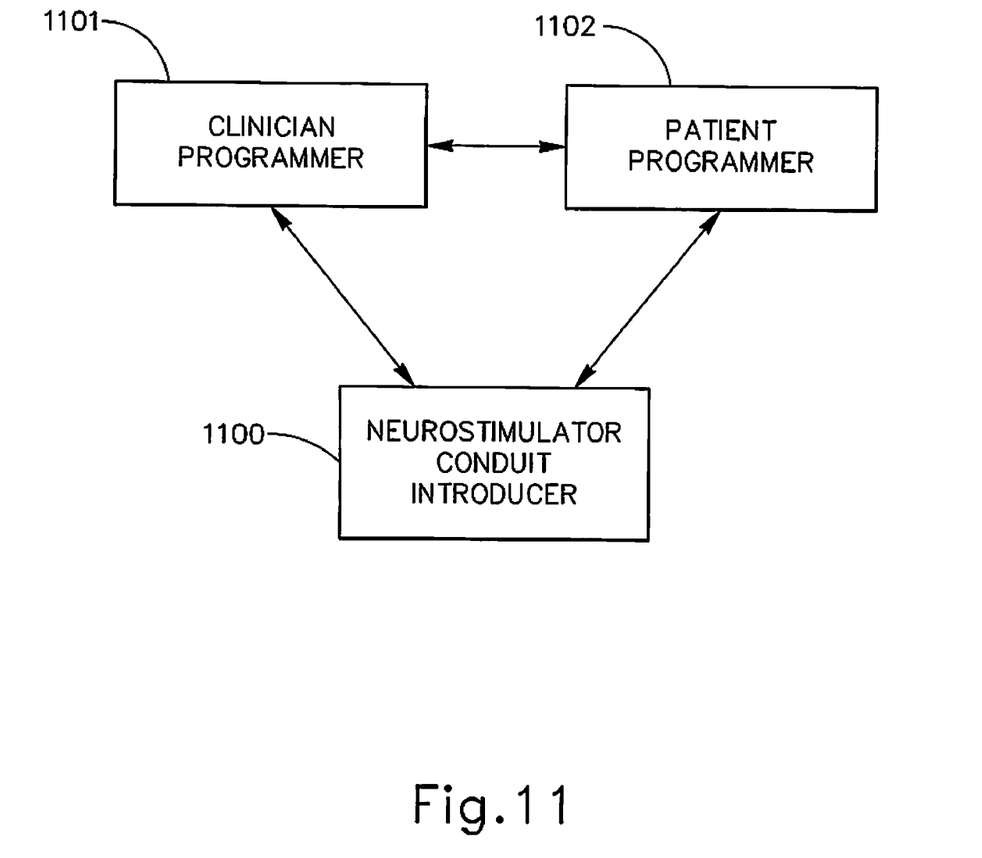
FIG. 11 is a block drawing illustrating the components of a neurostimulation system.

FIG. 11 illustrates other optional components may be used in conjunction with the exemplary neurostimulator conduit introducer 1100. For example, a clinician programmer 1101 and a patient programmer 1102 may be used. The clinician programmer 1101 may be a handheld computing device that permits a clinician to program spinal cord stimulation therapy for patient, for example, using input keys and a display. For example, using the clinician programmer 1101, the clinician may specify spinal cord stimulation parameters for use in delivery of spinal cord stimulation therapy.

The clinician programmer 1101 supports radio frequency telemetry with neurostimulator 1100 to download spinal cord stimulation parameters and, optionally, upload operational or physiological data stored by neurostimulator 1100. In this manner, the clinician may periodically interrogate neurostimulator 1100 to evaluate efficacy and, if necessary, modify the stimulation parameters.

Like the clinician programmer 1101, the patient programmer 1102 may be a handheld computing device. The patient programmer 1102 may also include a display and input keys to allow the patient to interact with the patient programmer 1101 and the implantable neurostimulator 1100. In this manner, the patient programmer 1101 provides the patient with an interface for control of spinal cord stimulation therapy by the neurostimulator 1100. For example, the patient may use the patient programmer 1101 to start, stop or adjust spinal cord stimulation therapy. In particular, the patient programmer 1101 may permit the patient to adjust stimulation parameters, for example, duration, amplitude, pulse width, and pulse rate, within an adjustment range specified by the clinician via the clinician programmer.

The neurostimulator conduit introducer 1100, the clinician programmer 1101, and the patient programmer 1102 may communicate via wireless communication. The clinician programmer 1101 and the patient programmer 1102 may, for example, communicate via wireless communication with the neurostimulator 1100 using radiofrequency (RF) telemetry techniques known in the art. The clinician programmer 1101 and the patient programmer 1102 also may communicate with each other using any of a variety of local wireless communication techniques, for example, radiofrequency (RF) communication according to the 802.11 or Bluetooth specification sets, or other standard or proprietary telemetry protocols.

Figure 12:
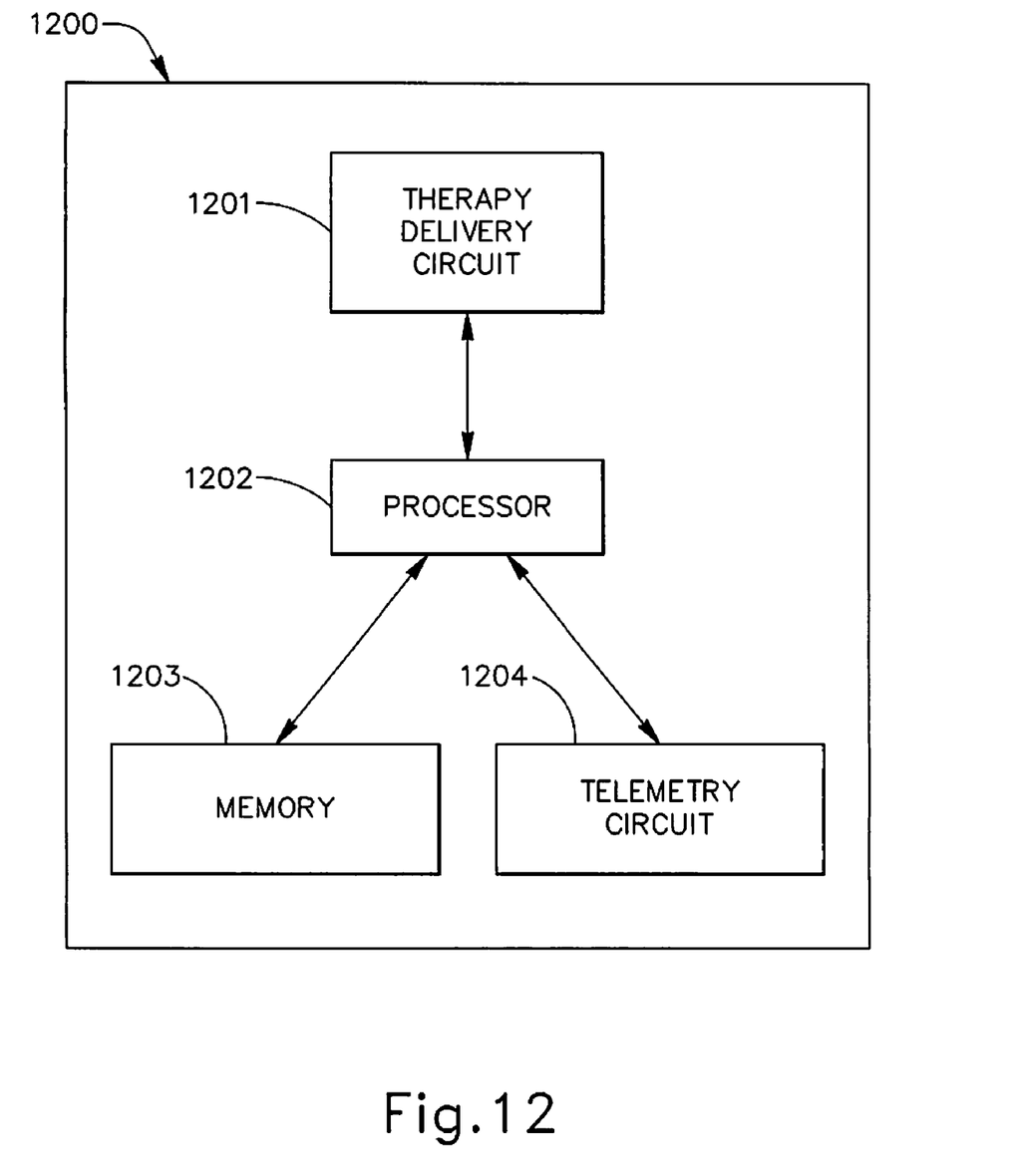
FIG. 12 is a block drawing illustrating the components of a neurostimulation system.

FIG. 12 illustrates other optional components of an exemplary neurostimulation system 1200. For example, the electrodes on the secondary leads are electrically coupled to a therapy delivery circuit 1201 via conductors within each secondary lead. The therapy delivery circuit 1201 may, for example, include an implantable pulse generator (not shown) coupled to a power source, for example, a battery. The implantable pulse generator within the therapy delivery circuit 1201 delivers electrical pulses to the patient via at least some of the electrodes under the control of a processor 1202.

The processor 1202 controls the implantable pulse generator within the therapy delivery circuit 1201 to deliver spinal cord stimulation therapy according to selected stimulation parameters. Specifically, the processor 1202 controls the therapy delivery circuit 1201 to deliver electrical pulses with selected amplitudes, pulse widths, and rates specified by the programs.

The processor 1202 may also include a microprocessor, a controller, a DSP, an ASIC, an FPGA, discrete logic circuitry, or the like. The neurostimulation system may also include a memory 1203. In some embodiments, the memory 1203 stores multiple sets of stimulation parameters that are available to be selected by the patient for delivery of spinal cord stimulation therapy. For example, the memory 1203 may store stimulation parameters transmitted by the clinician programmer 1101.

The memory 1203 may also store program instructions that, when executed by the processor 1202, cause the neurostimulator conduit introducer to deliver spinal cord stimulation therapy. The memory 1203 may include any volatile or non-volatile media, for example, a RAM, ROM, CD-ROM, NVRAM, EEPROM, flash memory, and the like. Accordingly, computer-readable media storing instructions may be provided to cause the processor to provide functionality as described herein.

A telemetry circuit 1204 may support wireless communication between neurostimulator conduit introducer 1100, the clinician programmer 1101, and the patient programmer 1102. In addition, in some embodiments, the telemetry circuit 1204 may support wireless communication with one or more wireless sensors that sense physiological signals and transmit the signals to the neurostimulator conduit introducer 1100.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems and leads for neurostimulation, as described herein. Also, the exemplary neurostimulator conduit introducer described herein may have a variety of neurostimulation applications, as well as possible applications in other electrical stimulation contexts, for example, delivery of cardiac electrical stimulation, including paces, pulses, and shocks, delivery of peripheral nerve stimulation, vascular surface treatment, and the like.

As such, the neurostimulator conduit introducer, as described herein, may be used, for example, as a spinal cord stimulator, a pelvic nerve stimulator, a deep brain stimulator, a gastrointestinal stimulator, a peripheral nerve stimulator, or a muscle stimulator. Further, neurostimulation may be used in different therapeutic applications, such as cardiac stimulation, deep brain stimulation, spinal cord stimulation, pelvic stimulation for pelvic pain, incontinence, or sexual dysfunction, gastric stimulation for gastroparesis, obesity or other disorders, or peripheral nerve stimulation for pain management. Neurostimulation also may be used for muscle stimulation, for example, functional electrical stimulation to promote muscle movement or prevent atrophy.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

What is claimed is:

1. A neurostimulator conduit introducer comprising:
    a solid central lead having a proximal end and a distal end;
    one or more secondary leads each having a proximal end and a distal end,
        wherein each of the one or more secondary leads is independently wrapped around the solid central lead,
        wherein each of the one or more secondary leads comprise an electrode located on distal end of each of the one or more secondary leads,
        wherein the electrode comprises an interior concave surface that is complementary to a surface of the solid central lead and an exterior surface comprising one or more planar surfaces; and
    a biocompatible conduit enclosing the solid central lead and the one or more secondary leads,
        wherein the biocompatible conduit is movable toward the proximal ends of the solid central lead and the one or more secondary leads to expose a part of the solid central lead and a part of the one or more secondary leads.

2. The neurostimulator conduit introducer of claim 1, wherein the neurostimulator is a spinal cord stimulator, a pelvic nerve stimulator, a deep brain stimulator, a gastrointestinal stimulator, a peripheral nerve stimulator, a vascular stimulator, or a muscle stimulator.

3. The neurostimulator conduit introducer of claim 2, wherein the neurostimulator is a spinal cord stimulator.

4. The neurostimulator conduit introducer of claim 1, wherein each of the one or more secondary leads has a different length.

5. The neurostimulator conduit introducer of claim 1, wherein the biocompatible conduit is movable toward the distal ends of the solid central lead and the one or more secondary leads to cover a part of the solid central lead and a part of the one or more secondary leads.

6. The neurostimulator conduit introducer of claim 1, wherein the proximal end of the solid central lead is coiled inside the biocompatible conduit, the proximal end of each one or more secondary leads is coiled inside the biocompatible conduit, or both the proximal end of the solid central lead and the proximal end of each one or more secondary leads are each independently coiled inside the biocompatible conduit.

7. The neurostimulator conduit introducer of claim 1, further comprising a battery coupled to the electrodes.

8. The neurostimulator conduit introducer of claim 7, wherein the battery is rechargeable.

9. The neurostimulator conduit introducer of claim 7, wherein the battery comprises a capacitor, a microchip, or a combination thereof.

10. A method of implanting a neurostimulator conduit introducer in the epidural space of a mammal comprising:
  inserting a neurostimulator conduit introducer comprising:
    a solid central lead having a proximal end and a distal end;
    one or more secondary leads each having a proximal end and a distal end,
      wherein each of the one or more secondary leads is independently wrapped around the solid central lead,
      wherein each of the one or more secondary leads comprise an electrode located on distal end of each of the one or more secondary leads,
      wherein the electrode comprises an interior concave surface that is complementary to a surface of the solid central lead and an exterior surface comprising one or more planar surfaces; and
    a biocompatible conduit enclosing the solid central lead and the one or more secondary leads,
      wherein the biocompatible conduit is movable toward the proximal ends of the solid central lead and the one or more secondary leads to expose a part of the solid central lead and a part of the one or more secondary leads; and
  guiding the neurostimulator conduit introducer into a desired position.

11. The method of claim 10, wherein the neurostimulator is a spinal cord stimulator, a pelvic nerve stimulator, a deep brain stimulator, a gastrointestinal stimulator, a peripheral nerve stimulator, a vascular stimulator, or a muscle stimulator.

12. The method of claim 11, wherein the neurostimulator is a spinal cord stimulator.

13. The method of claim 10, further comprising moving the biocompatible conduit toward the proximal ends of the solid central lead and the one or more secondary leads to expose a part of the solid central lead and a part of the one or more secondary leads.

14. The method of claim 10, further comprising moving the biocompatible conduit toward the terminal ends of the solid central lead and the one or more secondary leads to cover a part of the solid central lead and a part of the one or more secondary leads.

15. A kit comprising:
  a needle;
  a sterile drape;
  a neurostimulator conduit introducer comprising:
    a solid central lead having a proximal end and a distal end;
    one or more secondary leads each having a proximal end and a distal end,
      wherein each of the one or more secondary leads is independently wrapped around the solid central lead,
      wherein each of the one or more secondary leads comprise an electrode located on distal end of each of the one or more secondary leads,
      wherein the electrode comprises an interior concave surface that is complementary to a surface of the solid central lead and an exterior surface comprising one or more planar surfaces; and
    a biocompatible conduit enclosing the solid central lead and the one or more secondary leads,
    wherein the biocompatible conduit is movable toward the proximal ends of the solid central lead and the one or more secondary leads to expose a part of the solid central lead and a part of the one or more secondary leads; and
  suturing supplies.

* * * * *